US009758441B2

(12) United States Patent
Baird et al.

(10) Patent No.: US 9,758,441 B2
(45) Date of Patent: Sep. 12, 2017

(54) METHODS AND APPARATUSES FOR DEOXYGENATING PYROLYSIS OIL

(71) Applicant: UOP LLC, Des Plaines, IL (US)

(72) Inventors: Lance Awender Baird, Prospect Heights, IL (US); Timothy A. Brandvold, Arlington Heights, IL (US); Stanley Joseph Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 159 days.

(21) Appl. No.: 14/551,797

(22) Filed: Nov. 24, 2014

(65) Prior Publication Data

US 2016/0145172 A1    May 26, 2016

(51) Int. Cl.
| | |
|---|---|
| C10L 1/06 | (2006.01) |
| C07C 1/22 | (2006.01) |
| C07C 5/367 | (2006.01) |
| C10G 3/00 | (2006.01) |

(52) U.S. Cl.
CPC ............... *C07C 1/22* (2013.01); *C07C 5/367* (2013.01); *C10G 3/42* (2013.01); *C10G 3/47* (2013.01); *C07C 2521/04* (2013.01); *C07C 2521/06* (2013.01); *C07C 2523/42* (2013.01); *C07C 2523/44* (2013.01); *Y02P 30/20* (2015.11)

(58) Field of Classification Search
CPC .... C07C 1/20; C07C 1/24; C07C 1/22; C07C 1/00; C07C 7/04; C07C 5/367
USPC ............... 585/639, 640, 324, 240, 252, 250
See application file for complete search history.

(56) References Cited

U.S. PATENT DOCUMENTS

| | | | |
|---|---|---|---|
| 8,119,847 B2 * | 2/2012 | Dindi ....................... | B01J 23/78 585/240 |
| 8,546,635 B1 * | 10/2013 | Brandvold ............. | C10G 45/04 585/639 |
| 2009/0253947 A1 | 10/2009 | Brandvold et al. | |
| 2012/0151826 A1 | 6/2012 | Powell et al. | |
| 2013/0152453 A1 | 6/2013 | Baird et al. | |
| 2013/0324775 A1 | 12/2013 | Quignard et al. | |
| 2014/0000154 A1 | 1/2014 | Powell | |
| 2014/0031599 A1 | 1/2014 | Komplin et al. | |
| 2014/0088330 A1 | 3/2014 | Powell et al. | |
| 2014/0096764 A1 | 4/2014 | Komplin et al. | |
| 2014/0109464 A1 | 4/2014 | Powell et al. | |
| 2014/0135470 A1 | 5/2014 | Murray et al. | |

FOREIGN PATENT DOCUMENTS

| | | |
|---|---|---|
| AU | 2011253083 A1 | 11/2012 |
| IN | 201203441 | 8/2014 |
| WO | 2014090822 A1 | 6/2014 |
| WO | 2014146128 A1 | 9/2014 |

OTHER PUBLICATIONS

Rinaldi et al., Lignin into Arenes: A New Platform for the Production of Liquid Fules by Catalytic H-Transfer Reactions, Abstracts of Papers, 248th ACS National Meeting & Exposition, San Francisco, CA, United States, Aug. 10-14, 2014 (2014), ENFL-73 Publisher: American Chemical Society, Washington, D.C.
Dutta et al., Emerging Strategies for Breaking thet 3D Amorphous Network of Lignin, Catalysis Science & Technology (2014) Royal Society of Chemistry, Ahead of Print CODEN: CSTAGD; ISSN: 2044-4753.
Sooknoi et al., Xylenes Production from Renewable Feedstocks, Xylenes (2013), 33-55, Editor(s): Daramola, Michael Olawale, Publisher: Nova Science Publishers Inc., Hauppauge, N.Y.
Feng et al., Aqueous-Phase Hydrodeoxygenation of 4-propylphenol as a Lignin Model to N-propylbenzene over Rd-Ni/ZrO2 Catalysts, Journal of Molecular Catalysis A: Chemical (2014), 388-389, 41-46, Elsevier B.V.
Ramsurn et al., Deoxy-Liquefaction of Switchgrass in Supercritical Water with Calcium Formate as an In-Situ Hydrogen Donor, Bioresource Technology (2013), 143, 575-583, Elsevier Ltd.
Park et al., Production of Phenolics and Aromatics by Pyrolysis of Miscanthus, Fuel (2012), 97, 379-384, Elsevier Ltd.
Simonetti et al., Production of Monofuctional Hydrocarbons from Biomass Derived Carbohydrates viz Catalytic Conversion on Carbon Supported Platinum-Rhenium, Preprints-American Chemical Society, Division of Petroleum Chemistry (2009), 54(1), 35-38.

\* cited by examiner

*Primary Examiner* — Sharon Pregler

(57) ABSTRACT

Methods and apparatuses are provided for deoxygenating pyrolysis oil. A method includes contacting a pyrolysis oil with a deoxygenation catalyst in a first reactor at deoxygenation conditions to produce a first reactor effluent. The first reactor effluent has a first oxygen concentration and a first hydrogen concentration, based on hydrocarbons in the first reactor effluent, and the first reactor effluent includes an aromatic compound. The first reactor effluent is contacted with a dehydrogenation catalyst in a second reactor at conditions that deoxygenate the first reactor effluent while preserving the aromatic compound to produce a second reactor effluent. The second reactor effluent has a second oxygen concentration lower than the first oxygen concentration and a second hydrogen concentration that is equal to or lower than the first hydrogen concentration, where the second oxygen concentration and the second hydrogen concentration are based on the hydrocarbons in the second reactor effluent.

19 Claims, 1 Drawing Sheet

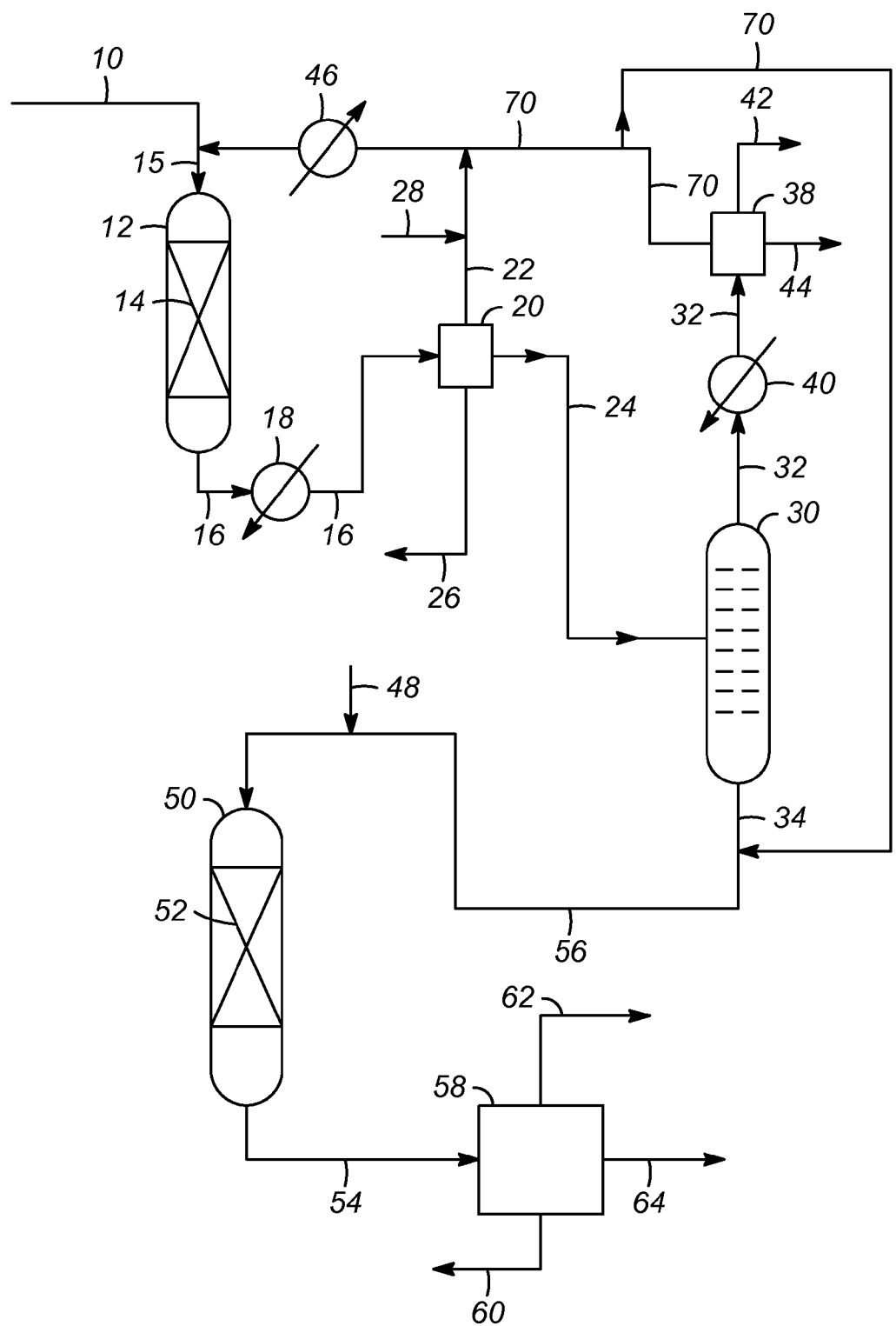

METHODS AND APPARATUSES FOR DEOXYGENATING PYROLYSIS OIL

GOV. FUNDING STATEMENT

This invention was made with Government support under DE-EE0002879 awarded by the Department of Energy. The Government has certain rights in this embodiment.

TECHNICAL FIELD

The technical field generally relates to methods and apparatuses for producing biofuels, and more particularly relates to methods and apparatuses for producing quality biofuels from pyrolysis oil.

BACKGROUND

Natural organic matter, such as wood, agricultural waste, algae, and a wide variety of other feedstocks can be heated in the absence of oxygen to produce pyrolysis oil. The pyrolysis oil is produced from biomass in a pyrolysis reactor, so the pyrolysis oil is a renewable resource. Pyrolysis oil can be directly used as a fuel for some applications, such as certain boilers and furnaces, and it can also serve as a feedstock for the production of fuels in petroleum refineries. Pyrolysis oil has the potential to replace petroleum as the source of a significant portion of transportation fuels.

However, pyrolysis oil is a complex, highly oxygenated organic liquid having properties that currently limit its utilization as a biofuel. For example, biomass-derived pyrolysis oil has high acidity and a low energy density attributable in large part to oxygenated hydrocarbons. These oxygenated hydrocarbons can undergo secondary reactions during storage to produce undesirable compounds, such as oligomers, polymers, and other compounds that can block liquid transport operations. As used herein, "oxygenated hydrocarbons" or "oxygenates" are organic compounds containing hydrogen, carbon, and oxygen. Such oxygenated hydrocarbons in the pyrolysis oil include carboxylic acids, phenols, cresols, alcohols, aldehydes, etc. Hydrocarbons in conventional pyrolysis oil typically include about 30 weight percent or greater oxygen, and there may be more oxygen present in the form of water or other non-hydrocarbon compounds. The pyrolysis oil is more useful as a biofuel or as a raw material for many processes if the oxygenated hydrocarbons are deoxygenated by hydroprocessing. Such deoxygenation typically produces water, carbon monoxide, and/or carbon dioxide as well as a substantially oxygen-free hydrocarbon, and the water or carbon dioxide can then be removed from the hydrocarbon fraction (which may still be referred to as pyrolysis oil.)

Unfortunately, deoxygenating pyrolysis oil necessitates heating the oil to hydroprocessing reaction temperatures. The hydroprocessing reaction temperatures result in reactions in the pyrolysis oil that typically produce solids that plug or foul the processing catalyst in a deoxygenation (or hydroprocessing) reactor. The solids form on the hot equipment and on the deoxygenation catalyst, reduce the catalytic activity, and slow or block liquid flow through the deoxygenation reactor. The solids are often a glassy brown polymer or powdery brown char, and these solids limit the deoxygenation reaction duration because the catalyst and reactor must be periodically purged of solids. In some cases, the catalyst is stuck together by the polymer, and may need to be drilled out of the reactor for removal. Furthermore, complete deoxygenation of pyrolysis oil tends to hydrogenate the aromatics in the pyrolysis oil, which lowers the octane rating of the resulting naphtha.

Accordingly, it is desirable to provide methods and apparatuses for deoxygenating pyrolysis oil without plugging, or at least with reduced plugging, of the catalyst and deoxygenation reactor. In addition, it is desirable to provide methods and apparatuses that minimize hydrogenation of the pyrolysis oil during the deoxygenation process. Furthermore, other desirable features and characteristics of the present embodiment will become apparent from the subsequent detailed description and the appended claims, taken in conjunction with the accompanying drawing and this background.

BRIEF SUMMARY

Apparatuses and methods for producing hydrocarbons are provided. In an exemplary embodiment, a method includes contacting a pyrolysis oil with a deoxygenation catalyst in a first reactor at deoxygenation conditions to produce a first reactor effluent. The first reactor effluent has a first oxygen concentration and a first hydrogen concentration, based on hydrocarbons in the first reactor effluent, and the first reactor effluent includes an aromatic compound. The first reactor effluent is contacted with a dehydrogenation catalyst in a second reactor at conditions that deoxygenate the first reactor effluent while preserving the aromatic compound to produce a second reactor effluent. The second reactor effluent has a second oxygen concentration lower than the first oxygen concentration and a second hydrogen concentration that is equal to or lower than the first hydrogen concentration, where the second oxygen concentration and the second hydrogen concentration are based on the hydrocarbons in the second reactor effluent.

In another embodiment, a method includes deoxygenating a pyrolysis oil in a first reactor to produce a first reactor effluent, and separating a pyoil solvent from the first reactor effluent. The pyoil solvent is combined with the pyrolysis oil prior to deoxygenation of the pyrolysis oil. The first reactor effluent is simultaneously deoxygenated and dehydrogenated in a second reactor.

In yet another embodiment, an apparatus includes a first reactor adapted to house a deoxygenation catalyst. The deoxygenation catalyst includes a metal on a deoxygenation support, where the metal includes one or more of platinum, palladium, ruthenium, nickel, molybdenum, tungsten, and cobalt. The deoxygenation support includes one or more of an alumina support, a silica-alumina support, a zirconia support, and a titania support. A second reactor is fluidly coupled to the first reactor and is adapted to house a dehydrogenation catalyst. The dehydrogenation catalyst includes platinum, palladium, or a combination thereof on a dehydrogenation support with a modifier metal. The modifier metal includes one or more of rhenium, boron, aluminum, gallium, indium, thallium, silicon, germanium, tin, and lead

BRIEF DESCRIPTION OF THE DRAWINGS

Various embodiments will hereinafter be described in conjunction with the FIGURE, which is a schematic diagram of a pyrolysis processing method and apparatus for producing hydrocarbons from pyrolysis oil, in accordance with an exemplary embodiment.

DETAILED DESCRIPTION

The following detailed description is merely exemplary in nature and is not intended to limit the application or uses of the embodiment described. Furthermore, there is no intention to be bound by any theory presented in the preceding technical field, background, brief summary, or the following detailed description.

In accordance with various exemplary embodiments described herein, a pyrolysis oil is partially deoxygenated in a first reactor to produce a first reactor effluent. The pyrolysis oil is deoxygenated in the first reactor by contacting it with a deoxygenation catalyst at deoxygenation conditions. The first reactor effluent is contacted with a dehydrogenation catalyst in a second reactor where the first reactor effluent is simultaneously deoxygenated and dehydrogenated while preserving an aromatic compound in the first reactor effluent. Plugging and fouling are minimized by operating the first reactor such that the pyrolysis oil is only partially deoxygenated. Capital costs and operating expenses are minimized by completing the deoxygenation in a second reactor, so a third reactor is not needed. The first reactor effluent is dehydrogenated in the second reactor while it is deoxygenated, so a second reactor effluent includes olefins and aromatic components that increase the octane rating over a reactor effluent without olefins and aromatic components.

In accordance with an exemplary embodiment illustrated in the FIGURE, a pyrolysis oil stream 10 is introduced to a first reactor 12. The pyrolysis oil stream 10 includes pyrolysis oil produced from renewable sources, such as wood, crop residues, algae, etc. The pyrolysis oil stream 10 may be obtained by different modes of pyrolysis, including fast pyrolysis, vacuum pyrolysis, catalytic pyrolysis, slow pyrolysis or carbonization, etc. Examples of pyrolysis oil "as-produced" can contain up to about 1,000 to about 30,000 ppm total metals, about 15 to about 35 weight percent water that can have high acidity (e.g., total acid number (TAN) >150), and a solids content of from about 0.1 wt. % to about 5 wt. %. The pyrolysis oil stream 10 may include untreated (e.g. "as produced") pyrolysis oil in some embodiments, but in other embodiments the pyrolysis oil stream 10 may be filtered to reduce solids to about 100 parts per million by weight or less, or otherwise treated. However, in some embodiments the pyrolysis oil is selectively treated to reduce any or all of the above properties to a desired level. In an exemplary embodiment, the pyrolysis oil comprises an organic phase (i.e., oil comprising primarily oxygenated or non-oxygenated hydrocarbons along with any dissolved water) that has a residual oxygen content of from about 10 weight percent to about 50 weight percent, or from about 30 to about 50 weight percent, or from about 35 to about 45 weight percent of the organic phase in various embodiments.

In an exemplary embodiment, the pyrolysis oil stream 10 is about 90 weight percent pyrolysis oil or more, or about 50 weight percent pyrolysis oil or more, or about 30 weight percent pyrolysis oil or more in various embodiments. In some embodiments, petroleum-based material or other feedstocks may be combined with the pyrolysis oil in the pyrolysis oil stream 10.

The pyrolysis oil is a bio-based material produced from a renewable resource. There are legal incentives to use bio-based materials, so it may be desirable to test the pyrolysis oil stream 10 to verify it includes bio-based materials, and to determine the concentration of those bio-based materials. ASTM test method D6866-05, "Determining the Bio-based Content of Natural Range Materials Using Radiocarbon and Isotope Ratio Mass Spectrometry Analysis" measures the ratio of radioactive carbon 14 to non-radioactive carbon 12 ($^{14}C/^{12}C$ isotope ratio.) A sample is tested and compared to the $^{14}C/^{12}C$ isotope ratio of a standard. Bio-based materials are organic materials in which the carbon is incorporated into the bio-based material recently, on a geologic time scale. Plants fix carbon dioxide ($CO_2$) in the atmosphere using photosynthesis, and a small amount of the carbon atoms in the atmosphere are radioactive $^{14}C$. Energy from the sun contacts carbon in the atmosphere and creates a background level of $^{14}C$ that is incorporated into all living creatures. When a living creature dies, there is no more uptake of $^{14}C$, so the concentration of $^{14}C$ begins to decline as it radioactively decays. The half-life of $^{14}C$ is about 5,730 years, so bio-based materials retain close to the equilibrium concentration present in living organisms for some time. However, petroleum was formed millions of years ago, so petroleum products have essentially no $^{14}C$. Therefore, the amount of bio-based materials in the pyrolysis oil stream 10 can be determined by comparing the $^{14}C/^{12}C$ ratio to the background level. A background level of 100 pMC (percent modern carbon) was established based on the year 1950, but atmospheric nuclear testing has increased the $^{14}C$ concentration to a level of about 107.5 pMC today. Therefore, a product can be tested to determine the percent natural oil using the ASTM D6866-05 method. In various embodiments, the pyrolysis oil stream 10 has a pMC of about 32 or more (which is about 30% bio-based or more,) or about 54 or more (which is about 50% bio-based or more,) or about 86 or more (which is about 80% bio-based or more.)

The pyrolysis oil stream 10 is stored and provided at an initial temperature of from about 0° C. to about 100° C. in an exemplary embodiment. In other embodiments, the pyrolysis oil stream 10 is stored and provided at an initial temperature of about 15° C. to about 100° C., or from about 15° C. to about 50° C., or from about 15° C. to about 30° C. The relatively low temperature can help minimize polymerization prior to introduction to the first reactor 12, because polymerization occurs slower at lower temperatures. A pyoil solvent 70 is optionally combined with the pyrolysis oil stream 10 prior to introduction to the first reactor 12 in some embodiments, where the pyoil solvent 70 is described more fully below. The combination of the pyrolysis oil stream 10 and the pyoil solvent 70, as well as any other streams added to the pyrolysis oil stream 10, produce the first reactor feedstock 15.

The pyrolysis oil stream 10 is contacted with a deoxygenation catalyst 14 in the first reactor 12 at deoxygenation conditions to produce a first reactor effluent 16. As such, the first reactor 12 is adapted to house the deoxygenation catalyst 14. The first reactor 12 can be a continuous flow reactor, such as a fixed-bed reactor, a continuous stirred tank reactor (CSTR), a trickle bed reactor, an ebulliating bed reactor, a slurry reactor, or any other reactor known to those skilled in the art for deoxygenation. In an exemplary embodiment, the first reactor 12 is a fixed-bed reactor. The pyrolysis oil stream 10 is partially deoxygenated in the first reactor 12, such that a first oxygen concentration in the first reactor effluent 16 is from about 10 to about 25 weight percent oxygen, or from about 15 to about 22 weight percent oxygen, or from about 19 to about 21 weight percent oxygen in various embodiments, where the oxygen concentration is based on the hydrocarbons in the first reactor effluent 16. The first reactor effluent 16 also has a first hydrogen concentration based on the hydrocarbons in the first reactor effluent 16. The pyrolysis oil stream 10 includes aromatic and olefinic compounds, so the first hydrogen concentration is lower than if the first reactor effluent 16 was saturated. The aromatics in the pyrolysis oil stream 10 are not generally hydrogenated in the first reactor 12, so the first reactor effluent 16 includes an aromatic compound. Controlling the deoxygenation in the first reactor 12 such that the pyrolysis oil stream 10 is only partially deoxygenated helps to minimize polymerization and plugging, which are observed with more complete deoxygenation. However, the partial deoxygenation proceeds to a sufficient degree so that a second reactor (described below) can essentially fully deoxygenate the pyrolysis oil.

In an exemplary embodiment, the deoxygenation catalyst 14 includes a metal or a combination of metals, such as a base metal(s), a refractory metal(s), and/or a noble metal(s), such as platinum, palladium, ruthenium, nickel, molybdenum, tungsten, and/or cobalt. The metal(s) may be on a deoxygenation support that is a metal oxide, such as one or more of an alumina support, a silica-alumina support (amorphous or zeolitic), a zirconia support, and/or a titania support. In an exemplary embodiment, the deoxygenation support is titania. Other hydroprocessing catalysts known to those skilled in the art may also be used. The deoxygenation conditions include a reaction temperature of from about 100° C. to about 400° C., or from about 150° C. to about 350° C. in different embodiments. The reaction pressure is from about 2,000 to about 20,000 kilopascals (kPa), or from about 3,400 to about 17,000 kPa in various embodiments. In this description, indicated pressures are gauge as opposed to absolute unless otherwise indicated. The liquid hourly space velocity is determined on a basis of weight of the first reactor feedstock/weight of deoxygenation catalyst/hour ($hr^{-1}$). The liquid hourly space velocity may be from about 0.10 to about 2 $hr^{-1}$, and the deoxygenation reaction may consume about 1,000 to about 15,000 standard cubic feet of hydrogen per barrel of pyrolysis oil (SCF/B).

Some of the oxygen from the pyrolysis oil stream 10 is converted to water, and water becomes less soluble in the pyrolysis oil as the oxygenated hydrocarbon concentration decreases. Water can optionally be removed from the first reactor effluent 16 in a wide variety of manners. One or more separators can be used, and the temperature can be adjusted to better control the quantity of water separated. The solubility of water decreases in the first reactor effluent 16 as the temperature drops, so the amount of water removed in a separator depends somewhat on the temperature in the separator. The amount of residual water in the first reactor effluent 16 and other streams may affect the amount of secondary polymerization, so the amount of water may be adjusted to limit such secondary polymerization. The FIGURE illustrates several separators and temperature control devices that are optionally present, where zero, one, or more of each device may be used in various embodiments. In various embodiments, the first reactor effluent 16 exits the first reactor 12 and is cooled in a first chiller 18 to a temperature of from about 0° C. to about 60° C., or from about 30° C. to about 60° C., or from about 60° C. to about 140° C., or from about 140° C. to about 200° C. However, other temperatures are used in other embodiments, and the first chiller 18 may not be needed or present in all embodiments. The first reactor effluent 16 may include from about 10 weight percent to about 20 weight percent water in some embodiments.

The first reactor effluent 16 optionally enters a first separator 20. Fluids flow from one process to another, and when fluids flow from one process to another the process equipment is fluidly coupled. The first separator 20 produces a first recovered hydrogen stream 22, a first separated hydrocarbon stream 24, and a first water stream 26. The first separator 20 includes one or more separation vessels, fractionation columns, heaters, condensers, heat exchangers, pipes, pumps, compressors, controllers, and/or the like. In an exemplary embodiment and as illustrated, the first separator 20 is a high pressure three-phase separator. In this description, the process streams may be referred to with different terminology before and after a process to better clarify the process flow, but it should be understood that the original terminology is not abandoned. As such, the first reactor effluent 16 passes through the first separator 20 with the hydrocarbons primarily flowing into the first separated hydrocarbon stream 24. Therefore, the pyrolysis oil from the pyrolysis oil stream 10 is present in the first separated hydrocarbon stream 24, and hydrocarbons from the first reactor effluent 16 are also present in the first separated hydrocarbon stream 24. Therefore, when the first separated hydrocarbon stream 24 is processed, it can also be said that the pyrolysis oil and/or the first reactor effluent 16 is processed.

The temperature and water content of the first reactor effluent 16 determine if a first water stream 26 is produced, where the first separator 20 does not produce the first water stream 26 in some embodiments, such as when the first chiller 18 produces a temperature to from about 140 to about 200° C. The first separated hydrocarbon stream 24 includes the partially deoxygenated pyrolysis oil from the pyrolysis oil stream 10, organic compounds from the pyoil solvent 70, and may include some residual compounds such as water, hydrogen, carbon dioxide, etc. The first water stream 26 may be further treated to recover hydrocarbons and then disposed of, further processed, or otherwise used. The first recovered hydrogen stream 22 includes hydrogen and volatile hydrocarbons, which may be returned to the first reactor 12, such as with the pyoil solvent 70 or in a separate stream. A first make-up hydrogen stream 28 may also be added to the first reactor 12 such that sufficient hydrogen is present in the first reactor 12 for the deoxygenation reaction. The recovered hydrogen and make-up hydrogen can then be used in the deoxygenation reaction in the first reactor 12.

The first separated hydrocarbon stream 24 is fractionated in a fractionation unit 30 to produce a fractionation overhead stream 32 and a fractionation bottoms stream 34. The fractionation unit 30 may include one or more fractionation columns in various embodiments, and is operated at conditions such that the fractionation overhead stream 32 has a maximum boiling range of from about 190° C. to about 225° C., or a maximum boiling range of from about 200° C. to about 220° C. in different embodiments. The minimum boiling range depends on the hydrocarbons present, but may range from about −20° C. to about 150° C. in some embodiments, or from about 30° C. to about 150° C. in another embodiment, but other boiling range limits are also possible. The fractionation unit 30 is operated such that the fractionation bottoms stream 34 has a viscosity that is low enough to permit further processing, e.g., such that the fractionation bottoms stream 34 is flowable.

The fractionation overhead stream 32 is optionally cooled in a second cooler 40 and optionally separated in a second separator 38 to produce a second gas stream 42, a second water stream 44, and the pyoil solvent 70. As described above, the temperature of the fractionation overhead stream 32 can be adjusted to better control the water content in the pyoil solvent 70. The second cooler 40 may cool the fractionation overhead stream 32 to from about 0° C. to about 60° C., or from about 10° C. to about 50° C., or from about 60° C. to about 150° C. in various embodiments, but other temperature ranges can also be used. The temperature can vary depending on the desired water level in the pyoil solvent 70. The second gas stream 42 includes volatile organic compounds, and may include some residual hydrogen or carbon dioxide. The second gas stream 42 may be collected and used as a fuel, reformed to produce hydrogen, further processed or otherwise used. The second water stream 44 may be further treated to recover any remaining hydrocarbons, disposed of, or otherwise used. The pyoil solvent 70 is combined with the pyrolysis oil stream 10 to produce the first reactor feedstock 15, as described above, and then processed in the first reactor 12. Excess pyoil solvent 70 may be added to the fractionation bottoms stream 34 for further processing.

In various embodiments, pyoil solvent 70 is heated prior to combination with the pyrolysis oil stream 10 such that the first reactor feedstock 15 is at the desired temperature when introduced into the first reactor 12. The pyoil solvent 70 may be heated in a pyoil heater 46. For example, the temperature of the pyoil solvent 70 may be adjusted to from about 200° C. to about 450° C., or from about 300° C. to about 450° C., or from about 325° C. to about 425° C. in various embodiments. The pyoil solvent 70 and the pyrolysis oil stream 10 may be combined at a predetermined ratio, so the temperature of the pyoil solvent 70 and the pyrolysis oil stream 10 can be set to provide the desired temperature in the first reactor 12. The ratio of pyoil solvent 70 to pyrolysis oil stream 10 may be from about 2/1 to about 20/1, or from about 2/1 to about 5/1, or from about 3/1 to about 4/1 in various embodiments, so the first reactor feedstock 15 includes a greater quantity of pyoil solvent 70 than of the pyrolysis oil stream 10.

The pyoil solvent 70 is a low-molecular weight fraction of the pyrolysis oil that has been partially deoxygenated, recycled, and heated. As such, the pyoil solvent 70 has a lower concentration of reactive components that can undergo secondary polymerization to form solids, and contains some oxygen but less oxygen than the pyrolysis oil stream 10. By having some oxygen in the pyoil solvent 70, the pyrolysis oil stream 10 and the pyoil solvent 70 are miscible. The pyoil solvent 70 may be combined with the pyrolysis oil stream 10 immediately before introduction to the first reactor 12, so reactive components in the pyrolysis oil are not held at an elevated temperature for an extended period of time before deoxygenation. The short time period between when the pyrolysis oil stream 10 and the pyoil solvent 70 are combined and when the first reactor feedstock 15 contacts the deoxygenation catalyst 14 in the first reactor 12 is about 60 seconds or less, or about 20 seconds or less, or about 10 seconds or less in various embodiments, and this short time period can minimize the formation of polymers.

The formation of polymers is reduced by combining the pyoil solvent 70 with the pyrolysis oil stream 10 prior to deoxygenation, as noted by reduced production of glassy brown polymers or powdery brown char compared to deoxygenation of the pyrolysis oil stream 10 without the addition of pyoil solvent 70. The reduced formation of polymers increases the yield of desired hydrocarbons. The reduced formation of polymers also produces lower viscosities than when the pyrolysis oil stream 10 is deoxygenated without the presence of pyoil solvent 70. Greater run-times are also achieved with reduced polymer formation, because plugging from polymer build-up is delayed.

The fractionation bottoms stream 34 is optionally combined with a side cut from the pyoil solvent 70 to produce a second reactor feed stream 56 that flows to a second reactor 50 containing a dehydrogenation catalyst 52. The second reactor 50 is adapted to house the dehydrogenation catalyst 52. The second reactor feed stream 56 includes the fractionation bottoms stream 34, which flows from the pyrolysis oil stream 10, the first reactor effluent 16, and other upstream process streams, so these streams are contacted with the dehydrogenation catalyst 52 through the second reactor feed stream 56. The second reactor 50 may be any suitable reactor system known in the art, and may include, for instance, a batch reactor or continuous flow reactor, such as a fixed-bed reactor, a continuous stirred tank reactor (CSTR), a trickle bed reactor, an ebulliating bed reactor, a slurry reactor, or any other reactor known to those skilled in the art.

The second reactor feed stream 56 is deoxygenated in the second reactor 50 to produce a second reactor effluent 54, and the aromatic compound from the first reactor effluent 16 is preserved. Cycloparaffins in the second reactor feed stream 56 are dehydrogenated simultaneously with the deoxygenation reactions in the second reactor 50, and the second reactor feed stream 56 includes cycloparaffins in many embodiments. In various embodiments, the second reactor effluent 54 has a second oxygen concentration that is lower than the first oxygen concentration in the first reactor effluent 16. For example, the second oxygen concentration is about 1 weight percent oxygen, or about 5,000 parts per million by weight oxygen, or about 1,000 parts per million by weight oxygen, based on the hydrocarbons in the second reactor effluent 54 where the oxygen is present as oxygenated hydrocarbons. The second reactor effluent 54 also has a second hydrogen concentration that is about the same or lower than the first hydrogen concentration of the first reactor effluent 16. For example, the second hydrogen concentration may be about the same weight percent hydrogen as the first hydrogen concentration of the first reactor effluent 16, or the second hydrogen concentration may be lower than the first hydrogen concentration of the first reactor effluent 16, but the second hydrogen concentration is not a higher weight percent hydrogen than the first hydrogen concentration (where the percent hydrogen is based on the hydrogen within the organic components.) The equal or lower concentration of hydrogen indicates the second reactor effluent 54 includes the same or more aromatic compounds as the second reactor feed stream 56, and the aromatic compounds increase the octane value of naphtha derived from the second reactor effluent 54.

In an exemplary embodiment, the dehydrogenation catalyst 52 in the second reactor 50 includes platinum, palladium, or a combination thereof on a dehydrogenation support with a modifier metal, wherein the modifier metal comprises one or more of rhenium, boron, aluminum, gallium, indium, thallium, silicon, germanium, tin, and lead. In various embodiments, the platinum and/or palladium are present at from about 1 weight percent to about 0.01 weight percent, or from about 1 weight percent to about 0.2 weight percent, or from about 1 weight percent to about 0.5 weight percent, based on the total weight of the dehydrogenation catalyst 52. The dehydrogenation support is a metal oxide including one or more of an alumina support, a silica-alumina support, and a titania support. In some embodiments, the dehydrogenation support is a non-halided amorphous metal oxide, where the dehydrogenation support and the dehydrogenation catalyst 52 are non-acidic. In an exemplary embodiment, the dehydrogenation support is titania or alumina. The dehydrogenation support may include an alkali metal in some embodiments, where the alkali metal promotes non-acidic properties. The alkali metal may be present at from about 0.1 to about 2 weight percent, or from about 0.1 to about 1.5 weight percent in different embodiments, relative to the weight of the dehydrogenation catalyst 52.

Reaction conditions for the simultaneous deoxygenation and dehydrogenation with the preservation of the aromatic compound include a temperature of from about 300° C. to about 540° C., or from about 400° C. to about 520° C., or from about 475° C. to about 520° C. in various embodiments. The pressure may be from about 340 kPa to about 5,500 kPa, or from about 1,000 kPa to about 3,100 kPa in various embodiments. The second reactor feed stream 56 is deoxygenated and dehydrogenated in the presence of hydrogen, and a second hydrogen supply stream 48 may provide the hydrogen. The liquid hourly space velocity is from about 0.1 to about 3 $hr^{-1}$.

The second reactor effluent 54 includes more water than the second reactor feed stream 56, because water is formed during deoxygenation. The lower oxygen concentration of the hydrocarbons in the second reactor effluent 54 also lowers the water solubility in the organic phase. The second reactor effluent 54 may have water removed in a third separator 58 to produce a third water stream 60, a third gas stream 62, and a third pyrolysis stream 64. A portion of the third pyrolysis stream 64 may optionally be recycled to the second reactor 50 (not illustrated) to aid in temperature control. The third gas stream 62 includes excess hydrogen and any volatile hydrocarbons produced in the simultaneous deoxygenation and dehydrogenation. The third gas stream 62 may be recycled for the hydrogen, or this stream can be used as a fuel, further processed or otherwise used. The third water stream 60 may be further treated to remove remaining hydrocarbons, disposed of, or otherwise used. The third pyrolysis stream 64 is produced from the pyrolysis oil stream 10 by two reactors instead of three reactors, and includes olefins, aromatics, and other organic compounds in a renewable stream that includes low concentrations of oxygen.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

What is claimed is:

1. A method of producing hydrocarbons comprising the steps of:
    contacting a pyrolysis oil with a deoxygenation catalyst in a first reactor at partial deoxygenation conditions to produce a first reactor effluent with a first oxygen concentration from about 15 to about 25 weight percent oxygen and a first hydrogen concentration based on the hydrocarbons in the first reactor effluent, wherein the first reactor effluent comprise an aromatic compound; and
    contacting the first reactor effluent with a dehydrogenation catalyst in a second reactor at conditions that deoxygenate the first reactor effluent while preserving the aromatic compound to produce a second reactor effluent, wherein the second reactor effluent has a second oxygen concentration lower than the first oxygen concentration and a second hydrogen concentration that is equal to or lower than the first hydrogen concentration, wherein the second oxygen concentration and the second hydrogen concentration are based on the hydrocarbons in the second reactor effluent.

2. The method of claim 1 wherein contacting the first reactor effluent with the dehydrogenation catalyst comprises contacting the first reactor effluent with the dehydrogenation catalyst that comprises platinum, palladium, or a combination thereof on a dehydrogenation support, and wherein the dehydrogenation support comprises one or more an alumina support, a silica-alumina support, and a titania support.

3. The method of claim 2 wherein contacting the first reactor effluent with the dehydrogenation catalyst comprises contacting the first reactor effluent with the dehydrogenation catalyst wherein the dehydrogenation catalyst comprises a modifier metal, and wherein the modifier metal comprises one or more of rhenium, boron, aluminum, gallium, indium, thallium, silicon, germanium, tin, and lead.

4. The method of claim 2 wherein contacting the first reactor effluent with the dehydrogenation catalyst comprises contacting the first reactor effluent with the dehydrogenation catalyst comprising a modifier metal wherein the modifier metal comprises one or more of tin, indium rhenium, or gallium.

5. The method of claim 1 wherein contacting the first reactor effluent with the dehydrogenation catalyst comprises contacting the first reactor effluent with the dehydrogenation catalyst wherein the dehydrogenation catalyst comprises a dehydrogenation support, and the dehydrogenation support comprises a non-halided amorphous metal oxide.

6. The method of claim 1 wherein contacting the first reactor effluent with the dehydrogenation catalyst comprises contacting the first reactor effluent with the dehydrogenation catalyst wherein the dehydrogenation catalyst comprises from about 0.2 weight percent to about 1 weight percent platinum, palladium, or a combination thereof, based on a total weight of the dehydrogenation catalyst.

7. The method of claim 1 wherein contacting the first reactor effluent with the dehydrogenation catalyst comprises contacting the first reactor effluent with the dehydrogenation catalyst at a temperature of from about 400 degrees centigrade to about 540 degrees centigrade.

8. The method of claim 1 wherein contacting the first reactor effluent with the dehydrogenation catalyst comprises contacting the first reactor effluent with the dehydrogenation catalyst at a pressure of from about 1,000 kilopascals gauge to about 3,100 kilopascals gauge.

9. The method of claim 1 further comprising:
    fractionating the first reactor effluent to produce a pyoil solvent; and
    combining the pyoil solvent with the pyrolysis oil to form a first reactor feedstock prior to contacting the pyrolysis oil with the deoxygenation catalyst.

10. The method of claim 9 wherein combing the pyoil solvent with the pyrolysis oil comprises producing the first reactor feedstock with more of the pyoil solvent than the pyrolysis oil.

11. The method of claim 1 wherein contacting the pyrolysis oil with the deoxygenation catalyst comprises contacting the pyrolysis oil with the deoxygenation catalyst at a temperature of from about 150 degrees centigrade to about 350 degrees centigrade.

12. The method of claim 1 wherein contacting the pyrolysis oil with the deoxygenation catalyst comprises contacting the pyrolysis oil with the deoxygenation catalyst at a pressure of from about 3,400 kilopascals gauge to about 17,000 kilopascals gauge.

13. A method of producing hydrocarbons comprising the steps of:
    deoxygenating a pyrolysis oil in a first reactor to produce a first reactor effluent;

separating a pyoil solvent from the first reactor effluent;
reducing the formation of polymers by combining the pyoil solvent with the pyrolysis oil prior to deoxygenating the pyrolysis oil, wherein the pyrolysis oil stream and the pyoil solvent are miscible; and
simultaneously deoxygenating and dehydrogenating the first reactor effluent in a second reactor.

14. The method of claim 13 wherein combining the pyoil solvent with the pyrolysis oil comprises producing a first reactor feedstock comprising a greater quantity of the pyoil solvent than of the pyrolysis oil.

15. The method of claim 13 wherein combining the pyoil solvent with the pyrolysis oil comprises producing a first reactor feedstock comprising a pyoil solvent to pyrolysis oil ratio of from about 2:1 to about 5:1.

16. The method of claim 13 wherein simultaneously deoxygenating and dehydrogenating the first reactor effluent comprises contacting the first reactor effluent with a dehydrogenation catalyst, wherein the dehydrogenation catalyst comprises platinum, palladium, or a combination thereof and a modifier metal, wherein the modifier metal comprises one or more of rhenium, boron, aluminum, gallium, indium, thallium, silicon, germanium, tin, and lead.

17. The method of claim 13 wherein simultaneously deoxygenating and dehydrogenating the first reactor effluent comprises contacting the first reactor effluent with a dehydrogenation catalyst, wherein the dehydrogenation catalyst comprises a dehydrogenation support comprising a non-halided amorphous metal oxide.

18. The method of claim 13 wherein simultaneously deoxygenating and dehydrogenating the first reactor effluent comprises contacting the first reactor effluent with a dehydrogenation catalyst at a temperature of from about 300 degrees centigrade to about 520 degrees centigrade and a pressure of from about 1,000 kilopascals gauge to about 3,100 kilopascals gauge.

19. The method of claim 13 wherein deoxygenating the pyrolysis oil comprises contacting the pyrolysis oil with a deoxygenation catalyst at a temperature of from about 150 degrees centigrade to about 350 degrees centigrade and a pressure of from about 3,400 kilopascals gauge to about 17,000 kilopascals gauge.

* * * * *